United States Patent [19]

Mundy

[11] Patent Number: 4,656,127
[45] Date of Patent: Apr. 7, 1987

[54] METHOD OF DETECTING MUTATIONS IN DNA AND RNA

[75] Inventor: Christopher R. Mundy, Buckinghamshire, England

[73] Assignee: Amersham International plc., Buckinghamshire, England

[21] Appl. No.: 602,720

[22] Filed: Apr. 23, 1984

[30] Foreign Application Priority Data

Apr. 22, 1983 [GB] United Kingdom ................ 8311018

[51] Int. Cl.⁴ ........................ C12Q 1/68; C12N 15/00
[52] U.S. Cl. ......................................... 435/6; 935/78; 435/172.3
[58] Field of Search .............. 435/6, 29, 34, 91, 172.1, 435/172.3, 193, 199; 436/63, 94, 501; 536/27; 935/9, 10, 76, 77, 78

[56] References Cited

U.S. PATENT DOCUMENTS

| | | | |
|---|---|---|---|
| 4,351,901 | 9/1982 | Bahl | 935/78 X |
| 4,358,535 | 11/1982 | Falkow | 435/35 X |
| 4,521,509 | 6/1985 | Benkovic | 435/91 X |

OTHER PUBLICATIONS

Sági, J. et al, *Biochem. and Biophys. Res. Comm.*, vol. 95, No. 1, 1980, pp. 156–162.
Huang, L. H. et al, *Nucleic Acids Research*, vol. 10, No. 5, 1982, p. 1579.

*Primary Examiner*—Esther M. Kepplinger
*Assistant Examiner*—Jeremy Jay
*Attorney, Agent, or Firm*—Wenderoth, Lind & Ponack

[57] ABSTRACT

A method of detecting a mutation of a specific nucleotide base in a target nucleic acid chain comprises: (a) hybridizing a labelled probe to the target to form a hybrid in which one end of the probe is positioned adjacent the specific base; (b) adding a nucleotide derivative, e.g. a thionucleotide, under conditions to cause it to join to the end of the probe if it is complementary to the specific base; (c) digesting the hybrid using an exonuclease enzyme under conditions such that the nucleotide derivative protects the probe from digestion; and observing the presence or absence of label attached to the target. The method can be used to detect mutations even when these are not present at restriction enzyme cleavage sites, and does not require the preliminary steps of restriction digestion, gel electrophoresis and DNA (or RNA) blotting.

14 Claims, 8 Drawing Figures

EXAMPLE 1
TARGET PREPARATION

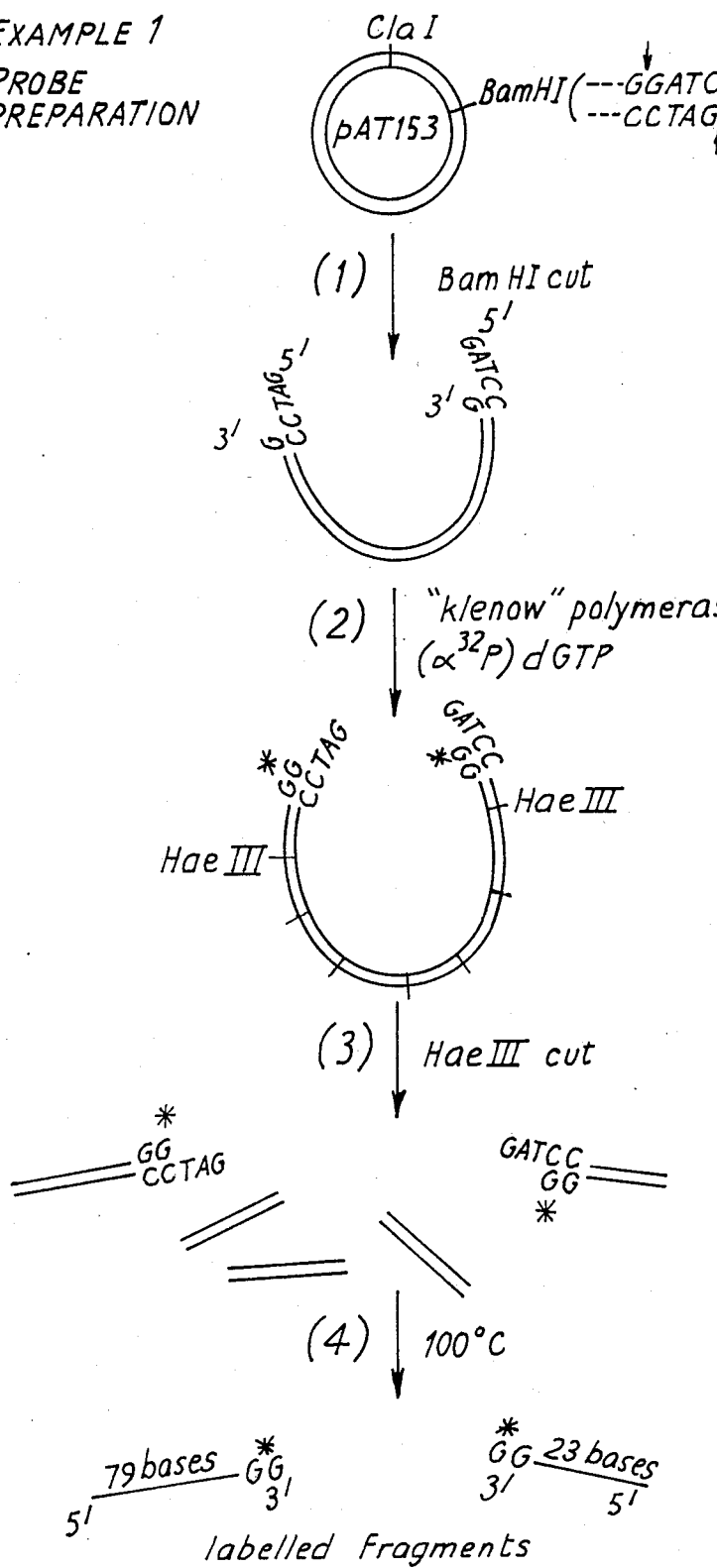

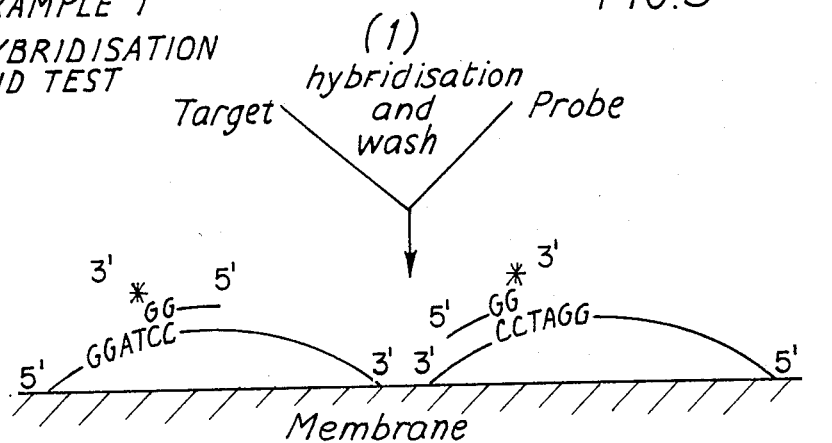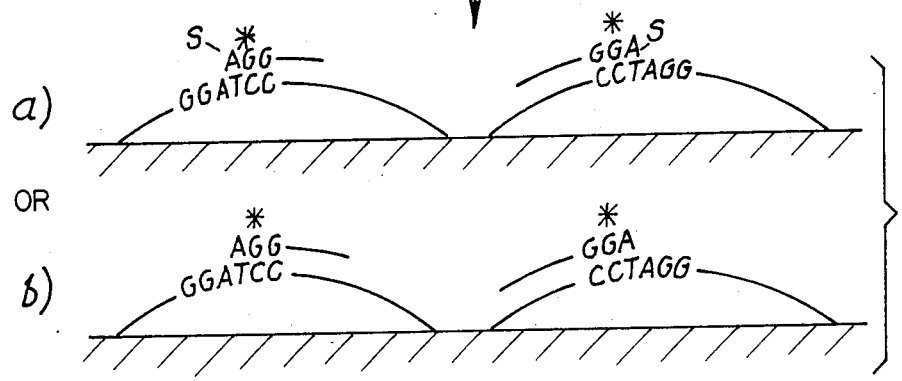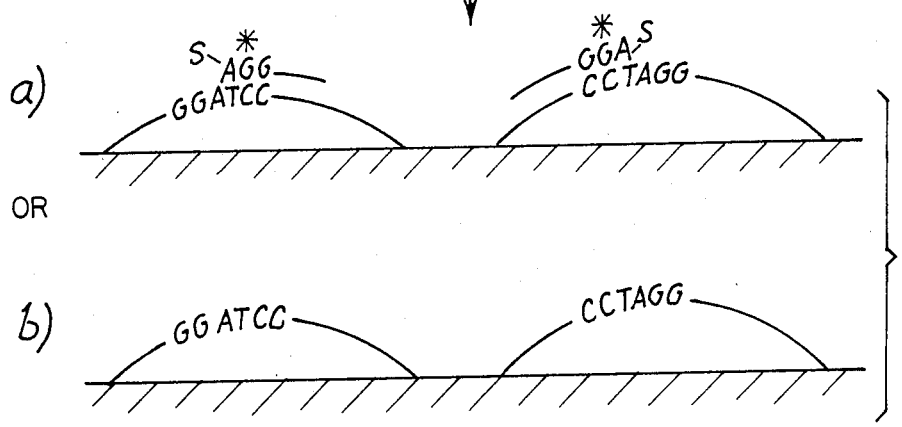
FIG. 3 — EXAMPLE 1 HYBRIDISATION AND TEST 1  2  3  4

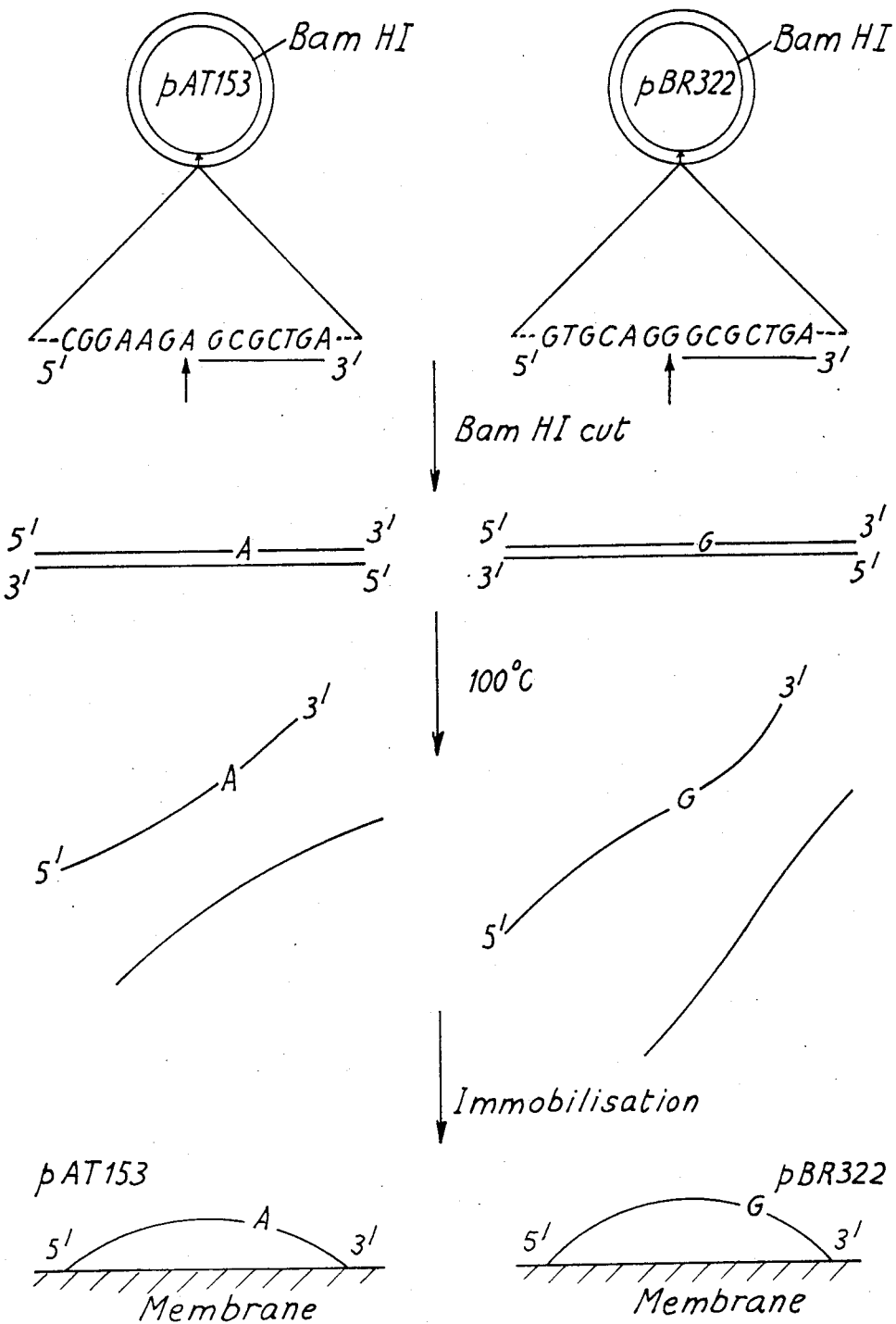

EXAMPLE 2
PROBE PREPARATION

FIG.6

Synthetic oligodeoxynucleotide (20 mer)

HO-G G A A A C G C G G A A G T C A G C G C
5'                                          3'

$\Big\downarrow$ T4 polynucleotide kinase $(\gamma\text{-}^{32}P)\,ATP$

```
*————————————
5'            3'
```

EXAMPLE 2
HYBRIDISATION AND TEST

FIG.7(CONT'D)
(3) Exonuclease III
a) 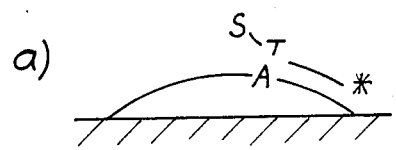
OR
b)  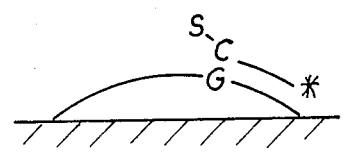
OR
c) 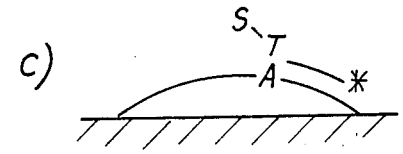
OR
d)  

METHOD OF DETECTING MUTATIONS IN DNA AND RNA

BACKGROUND OF THE INVENTION

The detection of mutations in DNA is of importance in a variety of fields. One such field is the diagnosis of genetically determined diseases and to identify carriers of such diseases. It has been estimated that, in Northern Europe, diseases caused by genetically determined defects may affect 1% of all live births. In some Mediterranean countries, 20% of the population are said to have genetic defects, associated with thalassaemia.

Conventional methods of gene analysis involve DNA isolation and restriction digestion, gel electrophoresis and DNA blotting by the technique of Dr. E. Southern, hybridization and washing, and finally autoradiography. A total of 3-10 days are required and radioactive probes are used for hybridization. Such methods are the subject of a review by P. F. R. Little in "Genetic Engineering" volume 1, pages 61-102, published 1981 by Academic Press.

Such methods can be used whether or not the DNA has been accurately sequenced in the region of interest. But they have major disadvantages; they are only effective to detect point mutations where these happen to be present in a restriction enzyme cleavage site, and then only provided that there are not other nearby cleavage sites for the same enzyme; they require the tedious preliminary steps of DNA isolation, restriction, gel electrophoresis, and Southern blotting; and they generally require the use of radioactive labels. These disadvantages have inhibited the development of genetic screening in clinical laboratories by these techniques.

When the DNA sequence in the region of interest is known, it is possible to overcome some of these disadvantages. B. J. Conner et al (Proc. Natl. Acad. Sci. U.S.A., 80, January 1983, 278-282) describe a method which does not require the mutation to be at a restriction enzyme cleavage site. A radioactively-labelled 19-base oligonucleotide probe is caused to hybridize with the region of the DNA which includes the possible mutation. The hybridization conditions are carefully chosen so that the probe does or does not hybridize depending on whether the mutation is or is not present. But the length of the probe and the hybridization conditions are difficult to get right and are critical for success. The aforesaid tedious preliminary steps are used, as is a radioactively labelled probe.

The method of the present invention generally requires a knowledge of the nucleic acid sequence in the region of interest. But it does not require the mutation to be at a restriction enzyme cleavage site. (In the case of mutations within restriction sites, it may be possible to infer the base change involved from a simple end-filling experiment, without needing to know the exact nucleic acid sequence). The method is capable of giving unambiguous results. In the preferred forms, it does not require the tedious preliminary steps that characterize prior methods, and it may not require the use of a radioactive label.

SUMMARY OF THE INVENTION

The present invention thus provides a method of detecting a mutation of a specific nucleotide base in a target nucleic acid chain by providing a linear probe complementary to a part of the nucleic acid chain extending in one direction from the specific base, (a) hybridizing the probe to the target to form a nucleic acid hybrid, whereby one end of the probe becomes hybridized to the nucleic acid chain substantially adjacent the specific base, (b) admixing with the hybrid a nucleotide derivative, under conditions appropriate for probe extension, so as to cause the nucleotide derivative to join on to the end of the probe only if the specific base in the target is, or is not, the mutation to be detected, a probe carrying said nucleotide derivative being resistant to digestion under particular conditions, (c) subjecting the hybrid to digestion under the said particular conditions whereby the double-stranded portion thereof is progressively digested starting at the said end of the probe unless the end has had said nucleotide derivative joined to it, (d) removing portions of the probe which are no longer hybridized to the nucleic acid chain, (e) and using the presence or absence of the probe remaining after digestion to detect a mutation of the specific nucleotide base, in the target.

Crucial to the method is step (b) which involves the use of a nucleotide derivative having a special property. When this nucleotide derivative is joined to the end of the probe, the probe is then resistant to digestion under particular conditions. In one alternative, a nucleotide derivative is mixed with the hybrid under conditions to cause it to join on to the end of the probe only if the specific base in the target is normal, i.e. not the suspected mutation. In another alternative, a (different) nucleotide derivative is mixed with the hybrid under conditions to cause it to join on to the end of the probe only if the specific base in the target is the suspected mutation. Various ways of achieving this are possible, and there will be described, designated A, B and C, of which embodiments A and B are preferred.

A. A probe is provided such that in step (a) one end becomes hybridized to the nucleic acid chain immediately adjacent the specific base. It is then possible to perform step (b) by admixing with the hybrid a nucleotide derivative under conditions appropriate for probe extension so as to cause the nucleotide derivative to join on to the end of the probe if it is complementary to the specific base.

B. A probe is provided such that in step (a) one end becomes hybridized to the nucleic acid chain a few bases away from the specific base. It is then possible to perform step (b) by admixing with the hybrid a nucleotide derivative, together with one or two other different nucleotides, under conditions appropriate for probe extension so as to cause them to join on to the end of the probe, including the nucleotide derivative if it is complementary to the specific base.

It may be helpful to illustrate embodiments of the invention where 1, 2 and 3 nucleotides are used in step (b).

A. The probe becomes hybridized in step (a) to the nucleic acid chain (the target) with its end base opposite the base immediately adjacent the specific base being tested for. We can consider by way of example a target having the sequence, in which * represents the point mutation ...AGAGĊTATGGATC... or ...AGAGṪTATGGATC...

The probe contains the sequence

```
    ATACCTAG...
3'
```

In step (a), the two become hybridized thus:

```
...AGAGĊTATGGATC...or...AGAGṪTATGGATC...
       ATACCTAG...          ATACCTAG...
    3'                   3'
``` in this preferred embodiment a derivative of guanosine (G) is used in step (b) without any other nucleotide and will be incorporated in one case but not the other:

```
...AGAGĊTATGGATC...or AGAGṪTATGGATC...
       GATACCTAG...       ATACCTAG...
    3'                 3'
```

B. The probe becomes hybridized in step (a) to the target with its 3'-end a few bases away from the specific base being tested for. With a target sequence as in A, we can consider a probe containing the sequence

```
    CCTAG...
3'
```

In step (a), the two become hybridized thus:

```
...AGAGĊTATGGATC...or...AGAGṪTATGGATC...
         CCTAG...            CCTAG...
      3'                  3'
```

In this embodiment, the derivative of guanosine (G) is used together with dATP and dTTP in step (b) to give the following

```
...AGAGĊTATGGATC...or...AGAGṪTATGGATC...
       GATACCTAG...       AATACCTAG...
    3'                 3'
```

It is easy to envisage comparable situations where the nucleotide derivative is used in admixture with one other nucleotide. It is however necessary in this embodiment that the nucleotide derivative be incorporated only opposite the specific base in the target.

C. A probe is provided such that in step (a) one end becomes hybridized to the nucleic acid chain immediately adjacent the specific base (as in A.), or a few bases away from the specific base (as in B). Step (b) can then be performed by:

(b)(i) admixing with the hybrid a chain-terminating nucleotide compound, optionally together with one or two other different nucleotides, under conditions appropriate for probe extension so as to cause the chain-terminating nucleotide compound to join on to the end of the probe if it is complementary to the specific base, (b)(ii) admixing with the resulting hybrid one or more nucleotide derivatives under conditions appropriate for probe extension so as to cause them to join on to the end of the probe if a chain-terminating nucleotide compound is not already present, a probe carrying said one or more nucleotide derivatives being resistant to digestion under particular conditions.

We can consider the same target/probe hybrid that was formed in step (a) of embodiment A above. A chain-terminating guanosine compound ($\overline{G}$) is used in step (b)(i) and will be incorporated in one case but not the other:

```
...AGAGĊTATGGATC...or...AGAGṪTATGGATC...
       G̲ATACCTAG...         ATACCTAG...
    3'                    3'
```

Then step (b)(ii) is performed with all four nucleotide derivatives (A, C, G, T) which will be incorporated in one case but not the other:

```
...AGAGĊTATGGATC...or...AGAGṪTATGGATC...
       G̲ATACCTAG...   ...TCTCAATACCTAG...
    3'
```

Clearly step (b)(ii) could have been performed using A, alone or together with C and optionally T. Suitable as chain-terminating nucleotide compounds are dideoxynucleotides and also several other nucleotide compounds which do not permit further addition of nucleotide to their 3' (or alternatively 5') end. They do not, however, protect the probe from digestion under chosen particular conditions.

It may be convenient to produce a probe as a restriction fragment when the site of the restriction cut is not immediately adjacent the site of mutation and one or two nucleotide types can be omitted to limit elongation.

The target and the probe may both be of DNA. Alternatively, either or both may be RNA.

In order to determine the presence or absence of probe in step (e) of the method, the probe will generally be labelled, for example with a radioactive isotope or with a group that takes part in an enzyme or fluorescent or chemiluminescent reaction.

In the method, the target may be immobilised or in solution. The use is preferred of an immobilised target, because that reduces the risk of complementary target strands re-hybridizing in step (a) and facilitates removal of unhybridized probe. However, use of a target in solution may be preferred on some occasions.

Crucial to be invention is the nucleotide derivative used in step (b) and the digestion conditions used in step (c). According to a preferred embodiment, a thionucleotide is used as the nucleotide derivative in step (b) and is caused to join on to the 3' end of the labelled probe. Then in step (c), digestion is effected using Exonuclease III, an enzyme from *E. coli* which digests double-stranded nucleic acid chains only from the 3' end, releasing deoxynucleoside-5'-mono-phosphates. This enzyme, if it does so at all, cleaves phospho-ester bonds when the phosphorus atom is linked to sulphur only at reduced efficiency. Thus a chain terminated with a thionucleotide at its 3' end is resistant to degradation by Exonuclease III.

Thus, in embodiments A and B above, a single thionucleotide is used in step (b). If that thionucleotide is complementary to the specific base of the target, it will join to the 3' end of the probe, and the resulting hybrid will be resistant to digestion in step (c) with Exonuclease III. If, on the other hand, the thionucleotide is not complementary to the specific base, it will not join the 3' end of the probe, and the hybrid will be digested in step (c).

DETAILED DESCRIPTION

If the nucleic acid to be investigated (the target) is not single-stranded, it must be made so. This can be done by conventional means such as heat denaturation of DNA. The single-stranded target chains are preferably immobilised e.g. on nitrocellulose. This pretreatment may be effected by spotting purified DNA onto nitrocellulose filters and baking at 80° C. to fix the single-stranded target, or possibly by direct processing of cells on nitrocellulose filters. It may not be necessary, though it may be advantageous, to subject the target to restriction digestion, gel electrophoresis and Southern blotting.

The linear probe may be of single- or double-stranded DNA; if double-stranded, it is converted to single-stranded form at the time of use. It is necessary that one end of a strand be complementary to a part of the target extending in one direction from, but not including, the specific base under investigation. Techniques for synthesising or otherwise providing such linear probes are known to those skilled in the field and will not be described here. The probe should be at least 10 nucleotides in length to ensure strong hybridization to the target, and may be as long as desired. Longer probes may be advantageous as they permit a larger amount of label per probe molecule and a higher degree of specificity of hybridization.

The nature of the label used to label the probe is not critical, save only that the label must not interfere with the digestion performed in step (c). Radioactive labels will often be convenient. Clinical laboratories will generally prefer non-radioactive labels, such as enzymes or chemiluminescent or fluorescent materials, and in such cases direct labelling may be possible, or labelling with a reporter molecule such as biotin.

It may be useful to design a probe with two polynucleotide sequences, one to hybridize to the target and the other to carry label. Provided that the label sequence has not become hybridized to the target in step (a), it does not matter whether or not the labelled bases are susceptible to digestion in step (c). Thus, if Exonuclease III is the enzyme used for digestion in step (c), a $^{35}$S-thionucleotide can be used as label only in a part of the probe sequence that will not become hybridized in step (a) to the target sequence. Similarly, label groups such as biotin or proteins may conceivably inhibit digestion in step (c).

If the probe is double-stranded, both strands will hybridize to their complementary strands of the target. Care must therefore be taken with labelling of a double-stranded probe. There are three alternatives for probe generation:

(i) A linear single-stranded uniformly labelled or end-labelled probe. This can be prepared by synthesising an oligonucleotide. Alternatively, labelled RNA probes can be prepared using phage SP6 RNA polymerase and a suitable template.

(ii) A linear double-stranded probe labelled only on the strand which hybridizes with its end adjacent the specific base under investigation. Such probes can be prepared, uniformly labelled, from an M 13 clone. Or they can be end-labelled in only one strand if the label intensity is found to be adequate. Or they can be labelled using T4 DNA polymerase.

(iii) A linear double-stranded probe labelled in both strands. Such probes can most conveniently be prepared but can give rise to problems of interpretation. One end, for example the 3' end, of one strand anneals to the target adjacent the specific base under investigation, and the 3' end of the other strand anneals at some other region of the target adjacent another base. It is preferable that this other base should be different from both the specific base under investigation and its expected mutant. When this other base is the same as either the specific base or its mutant, the method can still give useful information, but of a quantitative rather than a qualitative nature.

The labelled probe is first converted if necessary to a single-stranded form, and is then hybridized with the target to form a hybrid. After excess labelled probe has been removed by washing, the hybrid is subjected, under conditions appropriate for probe extension, e.g. polymerisation conditions, to reaction in embodiments A and B above with a nucleotide derivative optionally in the presence of one or two other different nucleotides, (or in embodiment C with a chain-terminating nucleotide compound). Hybridization, washing, and polymerisation conditions may be conventional.

However, any polymerase enzyme used must fulfil two requirements:

(i) The enzyme must be very faithful, i.e. must effect addition of one or more nucleotides to the end of the probe sequence if those nucleotides are complementary to the bases in the target sequence, but do so not at all or only at a very low frequency if they are not.

(ii) The enzyme must be free of exonuclease activity, i.e. must not tend to remove nucleotides from the end of the probe sequence.

One enzyme that meets these requirements is suitably purified calf thymus DNA polymerase. Others could readily be found, particularly among eukaryotic DNA polymerases, or among prokaryotic DNA polymerases that have been modified to remove unwanted exonuclease activity. Usually the same enzyme should be applicable, irrespective of whether the probe is of DNA or RNA.

The nucleotide derivative must also fulfil two requirements:

(i) In embodiments A and B above, it must join to the desired end of the labelled probe if, and only if, it is complementary to the specific nucleotide base. Thus if the specific nucleotide base is adenine, a derivative of thymidine or uridine would be suitable but a derivative of adenosine, cytidine or guanosine wound not. (In embodiment C, the job of detecting a mutation at the specific base of the target sequence is performed, not by a nucleotide derivative but by a chain-terminating nucleotide compound).

(ii) When joined to the end of the labelled probe, it must protect the resulting hybrid from digestion under conditions effective to digest hybrid not so protected.

The nucleotide derivative may in principle be a nucleotide which has been modified in the sugar, or in the base, or in the phosphate group that becomes involved in the phosphodiester bond. Many such modified nucleotides have been described in the literature. The nucleotide derivative needs to be chosen in conjunction with the exonuclease enzyme that is to be used in step (c).

As noted above, a suitable nucleotide derivative in some circumstances is one in which an oxygen atom attached to the alpha phosphorus atom has been replaced by sulphur, for example alpha-S-deoxythymidine triphosphate (alpha-SdTTP) or alpha-S-deoxyadenosine triphosphate (alpha-SdATP).

It may be possible to use a nucleotide derivative which is itself labelled. If a sufficiently high label density can be incorporated in the nucleotide derivative, then it may be possible to use a probe which has not been previously labelled, but which becomes labelled by attachment to it of the nucleotide derivative. This approach may be particularly useful when some preliminary purification of the target has been carried out. Non-specific label incorporation may occur in complex targets with palindromic regions.

In step (c), the resulting hybrid is subjected to digestion under conditions which (i) do not affect the labelled probe where this is protected at one end by the nucleotide derivative, and (ii) progressively digest the hybrid where the labelled probe is not so protected so as to remove it from the nitrocellulose or other medium on which the target has been immobilised.

The exonuclease enzyme is therefore one which: attacks double-stranded DNA, or DNA/RNA hybrids, or double-stranded RNA progressively from the 3' end; (alternatively, an enzyme could be used that attacks progressively from the 5' end); and is inhibited by the nucleotide derivative used in step (b).

As noted above an enzyme which can be used for the digestion is Exonuclease III. This enzyme attacks double-stranded DNA from 3' end only or DNA/RNA hybrid progressively from the 3' end of the RNA chain only. If there were used an exonuclease enzyme that digests double-stranded DNA or a DNA/RNA hybrid progressively from the 5' end, it would be necessary in step (b) to attach a nucleotide derivative at the 5' end of the labelled probe.

Where digestion proceeds progressively along the chain, it must be continued for long enough to remove most or all the label of the labelled probe from the immobilised target. This factor may place a limit on the maximum length of the labelled probe that is complementary to the target sequence and so becomes hybridized to the target.

When the method of this invention is performed with the target sequence in solution rather than immobilised, step (a) involves mixing the target material, denatured if necessary to present it in single-stranded form, with the probe material and then maintaining conditions, which effect hybridization. An extra enzyme may be included in step (c) to digest any single-stranded probe or target sequences present, but without digesting double-stranded sequences; RNase enzymes are available for this purpose when an RNA probe is used. It is then a simple matter in step (d) to remove non-hybridized portions of probe, since they have been broken down in step (c) to single nucleotides.

In all cases, after removal of non-hybridized portions of probe in step (d), the label still attached to the target is determined. This may be done by conventional methods depending on the nature of the label. If desired, the label may be eluted from the target in order to assist determination.

BRIEF DESCRIPTION OF THE DRAWINGS

Reference is directed to the accompanying drawings, in which:

FIGS. 1 to 3 are reaction schemes relating to Example 1 and showing respectively target preparation, probe preparation, and hybridization and test;

FIGS. 5 to 7 are reaction schemes relating to Example 2 and showing respectively target preparation, probe preparation, and hybridization and test.

The following Examples 1 and 2 illustrate the invention. The description of Examples 1 and 2 should be read in conjuction with, respectively, FIGS. 1 to 4 and FIGS. 5 to 8 of the drawings.

DESCRIPTION OF THE PREFERRED EMBODIMENTS

Example 1

Aims:

1. To demonstrate the ability of E. coli Exonuclease III to digest probe which has been hybridised to an immobilised target.

2. To demonstrate inhibition of Exonuclease III by an incorporated thionucleotide.

Figure 1:
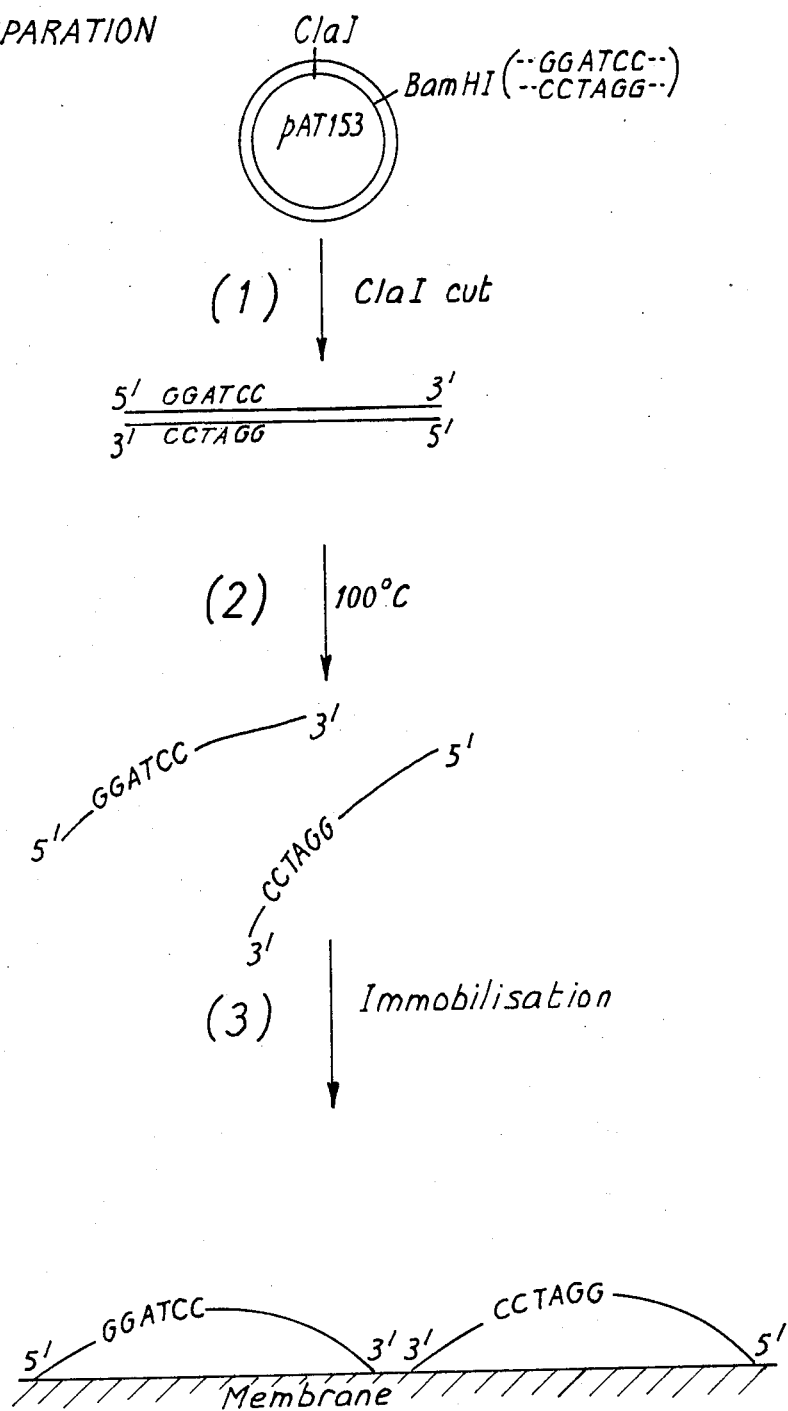

Method:

Target preparation (FIG. 1)

1. A sample of plasmid pAT153 was linearised by digestion with restriction endonuclease Cla I, under the following conditions:

10 mM Tris HCl pH 7.4
10 mM $MgCl_2$
50 mM NaCl
100 micrograms/ml bovine serum albumin (BSA)

2. The linear double-stranded DNA was converted to single-stranded form by heating at 100° C. for 2 minutes.

3. 1 microliter aliquots (containing 10 ng of DNA) of the denatured linear pAT153 solution were spotted in pairs in a grid pattern on a single sheet of nitrocellulose membrane (Schleicher and Schull type BA85), such that the sheet of membrane could be cut into identical 1.5 $cm^2$ sections each of which contained one pair of spots. The sheet containing spots was air-dried and baked in vacuo at 80° C. for 2 hours.

The sequence surrounding the BamHI site of plasmid pAT153 was the region to which the probe was expected to hybridize.

Probe preparation (FIG. 2)

1. Plasmid pAT153 was digested with restriction endonuclease BamHI in 10 mM Tris-HCl pH 7.4, 50 mM NaCl, 10 mM $MgCl_2$, 1 mM dithiothreitol, 100 micrograms/ml BSA.

2. Both ends of digested molecules were expected to have recessed 3' termini which would incorporate a deoxyguanosine nucleotide in the presence of the "Klenow" fragment of E. coli DNA polymerase I. An extension reaction was conducted by adding 10 units of Klenow polymerase and 50 microcuries of (alpha-$^{32}P$)dGTP (3000 curies/mmole) to 100 microliters of the BamHI digestion mix from Step 1. This amount contained 4 micrograms of linear plasmid pAT153. The extension reaction was incubated at 20° C. for 15 minutes. Unlabelled dGTP was added to a final concentration of 100 micromolar, and the reaction was allowed to continue for a further 5 minutes at 20° C. to ensure completion of the extension. The mixture was then heated at 65° C. for 10 minutes to inactivate the Klenow polymerase.

3. The labelled DNA preparation was digested with restriction endonuclease HaeIII by addition of 20 units of this enzyme to the mix from Step 2 and incubation at 37° C. for 30 minutes. This step reduced the chance that the 5' end of a given probe molecule could obstruct extension of its 3' end by complete annealing to the target. The reaction was stopped by extraction with 100 microliters of a 1:1 mixture of buffered phenol and chloroform.

Unincorporated radioactivity was removed in the following way:

100 microliters of 4M ammonium acetate pH 4.5 and 400 microliters of ethanol were added to the aqueous phase. The mixture was chilled at −70° C. for 10 minutes, warmed to 37° C. for 2 minutes and spun in a microcentrifuge at room temperature for 10 minutes. Unincorporated nucleotide remained in the supernatant. The pellet was washed twice in 66% ethanol containing 666 mM ammonium acetate pH 4.5, and redissolved in 100 microliters of 10 mM Tris-HCl pH 7.5, 1 mM EDTA.

4. The probe preparation from Step 3 was denatured by heating at 100° C. for 2 minutes. The single-stranded labelled DNA fragments in the mixture were complementary to regions on either side of the BamHI site of the target.

Hybridization and test (FIG. 3)

1. The sheet of nitrocellulose membrane, which carried 96 pairs of spots of denatured target DNA, was shaken gently at 65° C. for 2 hours in 30 ml of
  6×standard saline citrate
  5×Denhardt's solution
  100 micrograms/ml yeast tRNA
  0.1% sodium dodecyl sulphate (SDS)
1×standard saline citrate (SSC)=
  0.15M NaCl
  0.015M Na$_3$ citrate
  pH 7.0
1×Denhardt's solution=
  0.02% (w/v) BSA
  0.02% (w/v) Ficoll
  0.02% (w/v) polyvinylpyrrolidone 10 microliters of freshly boiled probe mix (which contained approximately 400 ng of DNA and 10$^6$ dpm of $^{32}$P) was then added, and the mixture was shaken gently at 65° C. for 16 hours. The radioactive mixture was then discarded, and the nitrocellulose membrane was washed by gentle shaking at 65° C. for 30 minutes in 50 ml of 6×SSC, 5×Denhardt's solution, 0.1% SDS The membrane was then washed for 30 minutes at room temperature in the following solutions: twice in 2×SSC and once in 0.1×SSC. The membrane was stored at 4° C. in 2×SSC. 1.5 cm$^2$ sections of membrane which contained pairs of spots were washed in 50 mM Tris-HCl pH 7.8 prior to use.

2. Washed sections of membrane were placed in flat-bottomed cylindrical test tubes of cross-sectional area 2.8 cm$^2$. Calf thymus DNA polymerase-catalysed extension reactions were conducted in 300 microliters of
  50 mM Tris-HCl pH 7.8
  10 mM Mg Cl$_2$
  1 mM dithiothreitol
  500 micrograms/ml BSA containing 37.5 units of calf thymus DNA polymerase-alpha (supplied by Pharmacia P-L biochemicals). Nucleotides were present where applicable at a final concentration of 100 micromolar. Reactions were incubated at 37° C. for 2 hours.

dATP was supplied by Pharmacia P-L biochemicals. Alpha-SdATP was a mixture of both A and B isomers and was prepared at Amersham.

Following the polymerase extension reaction probe molecules which initially were labelled by addition of a $^{32}$P-deoxyguanosine nucleotide to the BamHI-generated 3'-terminus were expected to have been extended by one "A" residue if the reaction contained dATP or alpha-SdATP. Polymerase reactions were terminated by addition of 5M NaCl to a final concentration of 100 mM. (Calf thymus DNA polymerase is inhibited at high salt concentration.)

3. 200 units Exonuclease III were added where applicable and the reaction mixtures were incubated at 37° C. for 2 hours. Membrane sections were then washed separately in 30 ml 2×SSC, dried, and exposed to X-ray film with an intensifying screen at −70° C.

Following autoradiography, membranes were assessed for bound $^{32}$P by liquid scintillation counting.

Results

Figure 4:
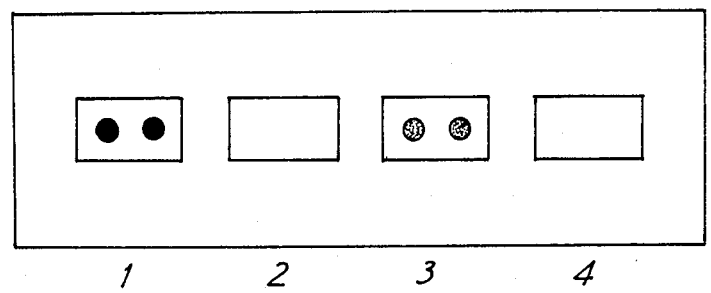
FIG. 4 is a representation of an autoradiograph showing the results obtained in Example 1.

FIG. 4 is a representation of an autoradiograph of four representative pairs of spots obtained under the following conditions:

1. DNA polymerase plus dATP used in step (2). No exonuclease used in step (3).

2. dATP used without polymerase in step (2). Exonuclease III used in step (3).

3. DNA polymerase plus alpha-SdATP used in step (2). Exonuclease III used in step (3).

4. DNA polymerase plus dATP used in step (2). Exonuclease III used in step (3).

The results indicate clearly that:

1. Exonuclease III has removed terminal label in the absence of incorporated thio-adenosine nucleotide.

2. Incorporation of thio-adenosine nucleotide has inhibited removal of label by Exonuclease III.

Liquid scintillation counting showed that approximately 14% of the label hybridized to control spots was retained following calf thymus DNA polymerase-alpha-catalysed extension in the presence of alpha-SdATP and digestion with Exonuclease III, compared to zero following extension in the presence of dATP and digestion with Exonuclease III.

Example 2

Aims:

1. To demonstrate Exonuclease III-catalysed removal of 5'-end-labelled probe from an immobilised target.

2. To demonstrate unequivocal discrimination of a "mutant" from a "wild-type" sequence.

Rationale:

Plasmid pAT153 lacks the segment of plasmid pBR322 from position 1648 to position 2353 bp (numbered from the EcoRI site). The base pair at position 1649 in pAT153 is A-T. That at position 1649 in pBR322 is G-C. Thus a probe with its 3' end at position 1648 will anneal to both pAT153 and pBR322, and will be adjacent to the point of "mutation".

Method:

Target preparation (FIG. 5)

1. Samples of plasmids pAT153 and pBR322 were digested separately with restriction endonuclease BamHI under the following conditions.

10 mM Tris HCl pH 7.8
10 mM MgCl$_2$
50 mM NaCl 100 micrograms/ml BSA

2. The linearised plasmids were heated to 100° C. for 2 minutes to separate their strands, and then transferred to an ice bath.

3. 0.5 microliter aliquots (containing 50 ng) of the denatured linear plasmid solutions were spotted in pairs in a grid pattern on nitrocellulose membrane (Schleicher & Schull type BA85), such that the membrane could be cut into identical 1.0 cm$^2$ sections, each of which contained one pair of pAT153 spots and one pair of pBR322 spots. Each 1 cm square was marked to distinguish the spots, and to permit cutting for separate liquid scintillation counting of pAT153 and pBR322 spots. The sheet containing spots was air-dried and baked in vacuo at 80° C. for 2 hours.

Probe preparation (FIG. 6)

An oligodeoxynucleotide was synthesised with the same sequence as one strand of pAT153 and pBR322 from position 1629 to position 1648 reading in the 5' to 3' direction. The solution phospho-triester method was used. This oligonucleotide was expected to hybridize to both plasmids with its 3' end adjacent to the point of divergence.

The 20-nucleotide probe was labelled with $^{32}P$ at its 5' end using T4 polynucleotide kinase and $(\gamma\text{-}^{32}P)ATP$ under standard conditions. The reaction mix contained 100 ng of oligodeoxynucleotide and 100 microcuries of $(\gamma\text{-}^{32}P)ATP$.

Unincorporated label was removed by selective precipitation of the oligonuceotide, by the method described in Example I, except that following addition of ammonium acetate and ethanol the mixture was chilled at −20° C. for 16 hours and at −70° C. for 15 minutes. Approximately 16% of applied label was incorporated.

Figure 7:
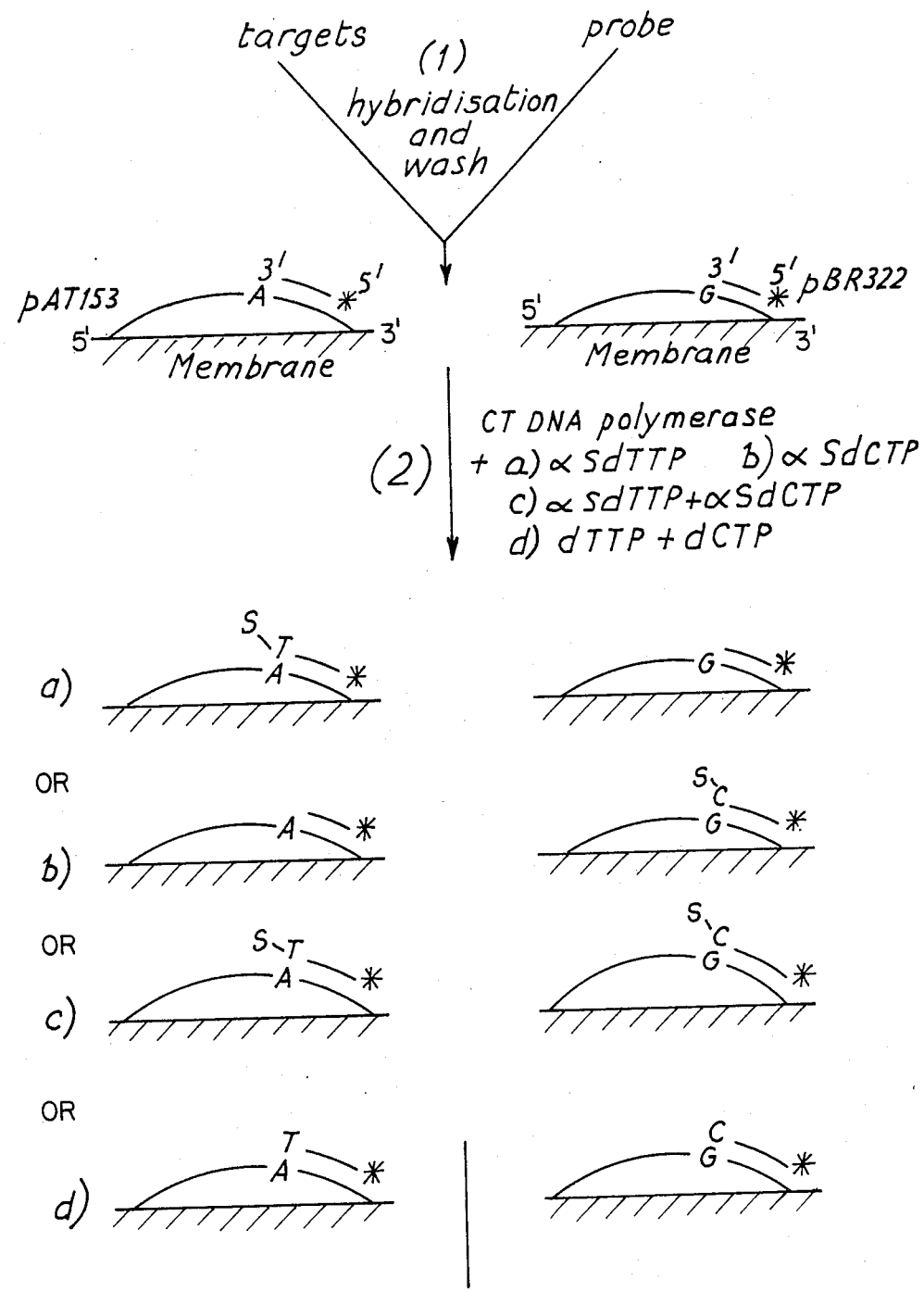

Hybridization and Test (FIG. 7)

1. The membrane sheet containing 24 sets of spots of denatured target DNA was shaken gently for 2 hours at 60° C. in 15 ml of 6×SSC, 5×Denhardt's solution, 100 micrograms/ml yeast tRNA, 0.1% SDS. 10 microliters of $^{32}P$-labelled probe mix, which contained approximately 5 ng of DNA and 10$^6$ dpm of $^{32}P$, was added, and the mixture was shaken gently at 60° C. for 16 hours.

The membrane was washed for 30 minutes at 60° C. in 50 ml of 6×SSC, 5×Denhardt's solution, 0.1% SDS; then twice at room temperature for 30 minutes in 100 ml of 2×SSC; and then once at room temperature for 30 minutes in 50 ml of 50 mM Tris-HCl pH 7.8. Membrane squares were cut from the sheet and used immediately, or stored at 4° C. in 2×SSC and re-washed in 50 mM Tris pH 7.8 prior to use.

2. Calf thymus DNA polymerase-alpha reactions were conducted in 300 microliters volume in flat-bottomed cylindrical polypropylene test tubes of cross-sectional area 2.8 cm$^2$. The reaction buffer was:

50 mM Tris-HCl pH 7.8
10 mM MgCl$_2$
1 mM dithiothreitol
500 micrograms/ml BSA

Calf thymus DNA polymerase-alpha fraction C, generously provided by Dr. A. M. Holmes of the Uniformed Services University of the Health Sciences, Bethesda, Md, USA, was used at a final concentration of 43 units/ml. Nucleotides were used when applicable at a concentration of 100 micromolar. The alpha-SdTTP stock contained approximately equal proportions of A and B isomers. The alpha-SdCTP stock contained >90% A isomer. Both stocks were prepared at Amersham.

Reactions were shaken at 37° C. on an oscillating shaker at 160 excursions per minute for 2 hours. Polymerase reactions were terminated by aspiration of the reaction mix and membrane squares were rinsed individually in 30 ml of 50 mM Tris-HCl pH 7.8.

3. Exonuclease III reactions were conducted in 300 microliter volume in the same tubes as those used for the polymerase reactions. The reaction mixtures contained: 50 mM Tris-HCl pH 7.8, 75 mM NaCl, 10 mM MgCl$_2$, 1 mM dithiothreitol, 500 micrograms/ml BSA, and 264 units/ml Exonuclease III (Pharmacia P-L biochemicals).

Reactions were shaken at 37° C. on an oscillating shaker at 160 excursions per minute for 30 minutes. Membrane squares were then washed in 30 ml 2×SSC, air dried, and exposed to X-ray film with an intensifying screen at −70° C. Following autoradiography, membrane squares were cut for separate determination of $^{32}P$ bound to pAT153 and pBR322 spots.

Results

Figure 8:
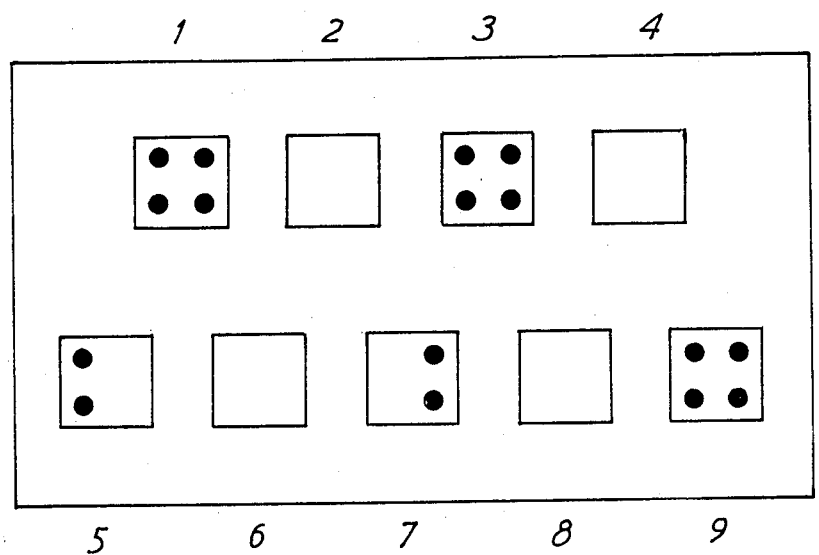
FIG. 8 is a representation of an autoradiograph showing the results obtained in Example 2.

FIG. 8 is a representation of an autoradiograph of nine representative sets of spots obtained under the following conditions. In each case, the left hand pair of spots is derived from pAT153 and the right hand pair from pBR322.

1. No polymerase in step (2). No exonuclease in step (3).

2. No polymerase in step (2). Exonuclease III used in step (3).

3. DNA polymerase plus dTTP and dCTP used in step (2). No exonuclease in step (3).

4. DNA polymerase plus dTTP and dCTP used in step (2). Exonuclease III used in step (3). (Scheme (d) of FIG. 7).

5. DNA polymerase plus alpha-SdTTP used in step (2). Exonuclease III used in step (3). (Scheme (a) of FIG. 7).

6. DNA polymerase plus dTTP used in step (2). Exonuclease III used in step (3).

7. DNA polymerase plus alpha-SdCTP used in step (2). Exonuclease III used in step (3). (Scheme (b) in FIG. 7).

8. DNA polymerase plus dCTP used in step (2). Exonuclease III used in step (3).

9. DNA polymerase plus alpha-SdTTP and alpha-SdCTP used in step (2). Exonuclease III used in step (3). (Scheme (c) of FIG. 7).

The results indicate clearly that:

1. Exonuclease III efficiently removes a 5'-end labelled 20-nucleotide probe at moderate enzyme concentration in a relatively short time.

2. The probe can be protected from Exonuclease III digestion by calf thymus DNA polymerase-catalysed incorporation of thionucleotide.

3. The method has unequivocally distinguished pAT153 and pBR322 on the basis of their different sequences using only the first base of the divergent sequence.

Liquid scintillation counting has shown that approximately 44% of $^{32}P$ label hybridized to control pAT153 spots was protected as a result of extension in the presence of alpha-SdTTP, and approximately 28% of label hybridized to control pBR322 spots was protected as a result of extension in the presence of alpha-SdCTP. Less than 5% of $^{32}P$ label hybridized to any pair of spots was protected by the presence of non-complementary thionucleotide.

I claim:

1. A method of detecting a mutation of a specific nucleotide base in a target nucleic acid chain by providing a linear probe complementary to a part of the nucleic acid chain extending in one direction from the specific base,
   (a) hybridizing the probe to the target to form a nucleic acid hybrid, whereby one end of the probe becomes hybridized to the nucleic acid chain substantially adjacent the specific base,
   (b) admixing with the hybrid a nucleotide derivative, under conditions appropriate for probe extension, so as to cause the nucleotide derivative to join on to the end of the probe only if the specific base in the target is, or is not, the mutation to be detected, a probe carrying said nucleotide derivative being resistant to digestion under particular conditions, wherein one of the probe and the nucleotide derivative is labelled,
   (c) subjecting the hybrid to digestion by an exonuclease enzyme under the said conditions whereby the double-stranded portion thereof is progressively digested starting at the said end of the probe unless the end has had said nucleotide derivative joined to it,
   (d) removing portions of the probe which are no longer hybridized to the nucleic acid chain,
   (e) and using the presence or absence of the probe remaining after digestion to detect a mutation of the specific nucleotide base in the target.

2. The method as claimed in claim 1, wherein the probe is provided such that in step (a) one end becomes hybridized to the nucleic acid chain immediately adjacent the specific base.

3. The method as claimed in claim 2, wherein step (b) is:
   (b) admixing with the hybrid a nucleotide derivative under conditions appropriate for probe extension so as to cause the nucleotide derivative to join on to the end of the probe if it is complementary to the specific base, a probe carrying said nucleotide derivative being resistant to digestion under particular conditions.

4. The method as claimed in claim 2, wherein step (b) is:
   (b)(i) admixing with the hybrid a chain-terminating nucleotide compound under conditions appropriate for probe extension so as to cause it to join on to the end of the probe if it is complementary to the specific base,
   (b)(ii) admixing with the resulting hybrid one or more nucleotide derivatives under conditions appropriate for probe extension so as to cause them to join on to the end of the probe if a chain-terminating nucleotide compound is not already present, a probe carrying said one or more nucleotide derivatives being resistant to digestion under particular conditions.

5. The method as claimed in claim 1, wherein the probe is provided such that in step (a) one end becomes hybridized to the nucleic acid chain a few bases away from the specific base.

6. The method as claimed in claim 5, wherein step (b) is:
   (b) admixing the hybrid a nucleotide derivative, together with one or two other different nucleotides, under conditions appropriate for probe extension so as to cause them to join on to the end of the probe, including the nucleotide derivative if it is complementary to the specific base, a probe carrying said nucleotide derivative being resistant to digestion under particular conditions.

7. The method as claimed in claim 5, wherein step (b) is:
   (b)(i) admixing with the hybrid a chain-terminating nucleotide compound, together with one or two other different nucleotides, under conditions appropriate for probe extension so as to cause them to join on to the end of the probe, including the chain-terminating nucleotide compound if it is complementary to the specific base,
   (b)(ii) admixing with the resulting hybrid one or more nucleotide derivatives under conditions appropriate for probe extension so as to cause them to join on to the end of the probe if a chain-terminating nucleotide compound is not already present, a probe carrying said one or more nucleotide derivatives being resistant to digestion under particular conditions.

8. The method as claimed in claim 1, wherein the target is DNA or RNA.

9. The method as claimed in claim 1, wherein the probe is labelled.

10. The method as claimed in claim 1, wherein the probe is DNA or RNA.

11. The method as claimed in claim 1, wherein the nucleotide derivative used in step (b) is a thionucleotide.

12. A method as claimed in claim 1, wherein there is used in step (c) an exonuclease enzyme that digests double-stranded nucleic acid chains only from the 3' ends.

13. The method as claimed in claim 1, wherein the probe extension is achieved by the addition of calf thymus DNA polymerase under polymerisation conditions.

14. A method as claimed in claim 1, wherein the target is immobilised.

* * * * *